United States Patent [19]

Gros et al.

[11] Patent Number: 4,479,006
[45] Date of Patent: Oct. 23, 1984

[54] PROCESS FOR THE PREPARATION OF 1-CARBAMOYL-3-(3,5-DICHLOROPHENYL)-HYDANTOINS

[75] Inventors: Georges Gros, Bourg la Reine; Marc Molin, Neuilly sur Marne, both of France

[73] Assignee: Rhone-Poulenc Agrochimie, Lyons, France

[21] Appl. No.: 554,382

[22] Filed: Nov. 22, 1983

Related U.S. Application Data

[63] Continuation of Ser. No. 260,175, May 4, 1981, abandoned.

[30] Foreign Application Priority Data

May 29, 1980 [FR] France ............................ 80 12238
Apr. 17, 1981 [FR] France ............................ 81 07962

[51] Int. Cl.$^3$ .................. C07D 233/80; C07D 233/82
[52] U.S. Cl. ............................................ 548/312
[58] Field of Search ............................ 548/312

[56] References Cited

U.S. PATENT DOCUMENTS 3,755,350 8/1973 Sauli .............................. 424/273 R

OTHER PUBLICATIONS

Kusuda et al., Chem. Abst., 1974, vol. 80, No. 3516k and 3519p.
Shibuya et al., Chem. Abst., 1979, vol. 90, No. 23040k.

Weber et al., Phase Transfer Catalysis in Organic Synthesis, Springer, Berlin, 1977, pp. 6 & 8.

*Primary Examiner*—Richard A. Schwartz
*Attorney, Agent, or Firm*—Browdy & Neimark

[57] ABSTRACT

1. Process for the manufacture of N-substituted 1-carbamoyl-3-(3,5-dichlorophenyl)-hydantoins of the formula:

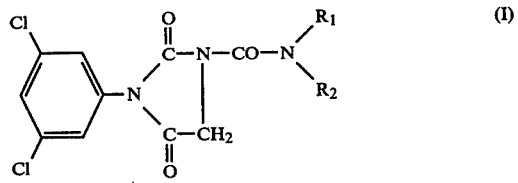

in which $R_1$=alkyl ($C_1$–$C_4$) or phenyl and $R_2$=H or alkyl ($C_1$–$C_4$).

2. This process comprises two steps:
   a. reacting phosgene with 3-(3,5-dichlorophenyl)-hydantoin in an inert organic solvent medium, in the presence of an acid acceptor, in order to form 1-chlorocarbonyl-3-(3,5-dichlorophenyl)-hydantoin, and
   b. reacting the chlorocarbonyl formed with an amine $HNR_1R_2$ in an inert organic solvent, in the presence of an acid acceptor.

3. This process makes it possible to obtain the products I, which can be used as agricultural fungicides, with good yields.

25 Claims, No Drawings

PROCESS FOR THE PREPARATION OF 1-CARBAMOYL-3-(3,5-DICHLOROPHENYL)-HYDANTOINS

This application is a continuation, of application Ser. No. 260,175, filed May 4, 1981, now abandoned.

The present invention relates to a new process for the manufacture of N-substituted 1-carbamoyl-3-(3,5-dichlorophenyl)-hydantoins and also to a new product, namely 1-chlorocarbonyl-3-(3,5-dichlorophenyl)-hydantoin, which can be used as a new intermediate in the manufacture of these products.

Certain N-substituted 1-carbamoyl-3-(3,5-dichlorophenyl)-hydantoins are known as plant-protection products, in particular as fungicides for agriculture. This applies particularly to 1-isopropylcarbamoyl-3-(3,5-dichlorophenyl)-hydantoin, commonly referred to as iprodione, which forms the subject of U.S. Pat. Nos. 3,755,350 and 3,823,240. This compound can be prepared in accordance with various processes. The above patents describe a method in which 3-(3,5-dichlorophenyl)-hydantoin is reacted with isopropylcarbamyl chloride, the latter being obtained by condensing phosgene with isopropylamine. However, this process gives rather unsatisfactory yields for an industrial scale operation. Now, the development of the abovementioned fungicides makes it necessary to develop a process which enables these products to be obtained under even more economical conditions. The present invention relates to a process which makes it possible to meet this requirement. It relates more especially to a process for the preparation, starting from 3-(3,5-dichlorophenyl)-hydantoin, of a compound of the formula:

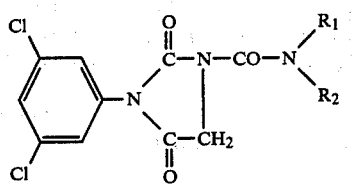

in which $R_1$ is an alkyl radical containing from 1 to 4 carbon atoms or the phenyl radical and $R_2$ is a hydrogen atom or an alkyl radical containing from 1 to 4 carbon atoms, which comprises:

in a first step, reacting phosgene with 3-(3,5-dichlorophenyl)-hydantoin in an inert organic solvent medium, preferably in the presence of an acid acceptor, in order to form 1-chlorocarbonyl-3-(3,5-dichlorophenyl)-hydantoin, in accordance with the equation:

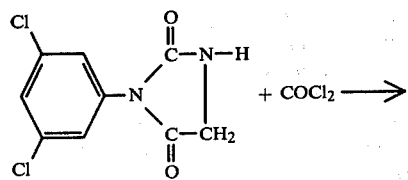

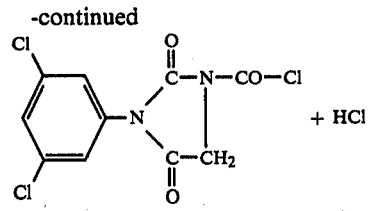

and, in a second step, reacting the resulting product with a primary or secondary amine of the formula $HNR_1R_2$, in which $R_1$ and $R_2$ have the meanings indicated above, in an inert organic solvent, in the presence of an acid acceptor, in accordance with the equation:

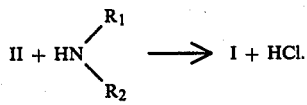

The first step, referred to as the phosgenation step, is preferably carried out with an excess of phosgene, relative to stoichiometry, in order to prevent the formation of the symmetrical urea resulting from the condensation of the compound of the formula II with the starting compound. However, the excess must not be too large, since the unreacted part of the phosgene must be degassed at the end of the reaction. Preferably, the reaction is carried out with an excess of 5 to 100 mol %.

This first step is preferably carried out in the presence of at least a stoichiometric amount of an acid acceptor, which in this case is a hydrochloric acid acceptor. This acceptor can be a strong organic base or an inorganic base.

The strong organic base which can be used is a tertiary amine, such as a trialkylamine, e.g. triethylamine, or a pyridine, such as pyridine and dimethylaminopyridine. This organic base is advantageously used in an approximately stoichiometric amount.

The inorganic base which can be used is an alkali metal carbonate or an alkali metal hydroxide, preference being given to the carbonate and in particular to disodium carbonate. This inorganic base can be used in a stoichiometric amount, but an excess which can range up to about 150% is preferred.

The acid acceptor according to the invention can advantageously be associated with an auxiliary agent. The latter can be either an auxiliary base or a transfer agent.

The auxiliary base, which is associated in an amount of 1 to 15% and preferably of 5 to 10%, is an organic base of the same type as that defined above, but different from the first. Pyridine, dimethylaminopyridine or triethylamine, in particular, can be used for this purpose.

The transfer agent which can be used in association with the acid acceptor, preferably when the latter is an inorganic base and in particular an alkali metal carbonate, is either an ammonium or phosphonium derivative or a sequestering agent, each of these types of compound being defined below.

The quaternary ammonium derivatives which can be used according to the present invention preferably correspond to the general formula:

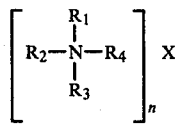

in which: $R_1$, $R_2$, $R_3$ and $R_4$, which are identical or different, each represent an alkyl radical containing from 1 to 20 carbon atoms, a cycloalkyl radical containing from 3 to 6 carbon atoms, an alkenyl radical containing from 2 to 20 carbon atoms or an optionally substituted phenylalkyl radical in which the alkyl part contains from 1 to 6 carbon atoms, X represents a chlorine, bromine or fluorine atom or an $SO_4$, $SO_4H$, $PO_4H_2$ or hydroxyl radical, an alkoxysulphonyloxy radical containing from 1 to 4 carbon atoms (such as methoxysulphonyloxy or ethoxysulphonyloxy), an alkanesulphonyloxy radical containing from 1 to 4 carbon atoms (such as methanesulphonyloxy or ethanesulphonyloxy), an arenesulphonyloxy radical (such as benzenesulphonyloxy or p-toluenesulphonyloxy) or an alkanoyloxy radical containing from 1 to 4 carbon atoms (such as acetyloxy and propionyloxy) and n is a number equal to the valency of X.

Good results have been obtained by using mixtures of quaternary ammonium derivatives such as those currently marketed under the following trademarks:

Adogen 464: a mixture of methyltrialkylammonium chlorides in which the alkyl parts contain from 8 to 10 carbon atoms, and Cemulcat K 012: a mixture of dihydroxyethyldialkylammonium chlorides in which the alkyl parts contain from 16 to 18 carbon atoms.

The catalysts which are preferably used are ammonium derivatives of the formula:

in which: X and n have the same meaning as in the foregoing formula and $R_5$ represents an alkyl radical containing from 1 to 4 carbon atoms, such as ethyltributylammonium chloride, methyltributylammonium chloride, tetrabutylammonium chloride or tetrabutylammonium bisulphate.

The phosphonium derivatives which can be used according to the present invention preferably correspond to the formula:

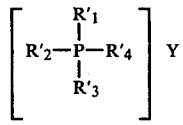

in which: $R'_1$, $R'_2$, $R'_3$ and $R'_4$, which are identical or different, each represent an alkyl radical containing from 2 to 8 carbon atoms and Y represents a chlorine or bromine atom.

The amount of these derivatives can vary within very wide limits ranging from 0.01 mol to 1 mol per equivalent of basic agent used. In practice, for economic reasons, from 0.5 to 5 mol % of phosphonium derivative is used per mol of main reactant.

The alkali metal carbonates can also be used advantageously in association with a sequestering agent, which is in itself known, of the formula:

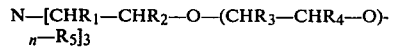

in which: n is an integer which is greater than or equal to 0 and less than or equal to about 10 ($0 \leq n \leq 10$), $R_1$, $R_2$, $R_3$ and $R_4$, which are identical or different, represent a hydrogen atom or an alkyl radical having from 1 to 4 carbon atoms and $R_5$ represents an alkyl or cycloalkyl radical having from 1 to 12 carbon atoms, a phenyl radical or a radical $—C_mH_{2m}—\phi$ or $C_mH_{2m+1}—\phi—$, in which m is between 1 and 12.

It is preferred to use a sequestering agent in the formula of which $R_1$, $R_2$, $R_3$ and $R_4$ represent a hydrogen atom or a methyl radical, $R_5$ having the above meaning and preferably being an alkyl radical having 1 to 4 carbon atoms, and n having the above meaning and preferably being at least zero and at most 3.

The following may be mentioned: tris-(3-oxaheptyl)-amine of the formula:

N—(CH$_2$—CH$_2$—O—C$_4$H$_9$)$_3$, tris-(3,6-dioxaheptyl)-amine of the formula:

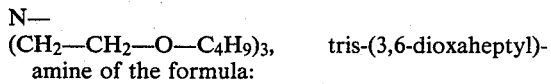
tris-(3,6,9-trioxadecyl)-amine of the formula:

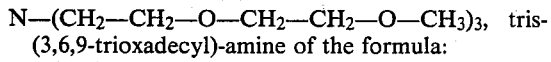
tris-(3,6-dioxaoctyl)-amine of the formula:

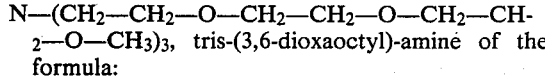
tris-(3,6,9-trioxaundecyl)-amine of the formula:

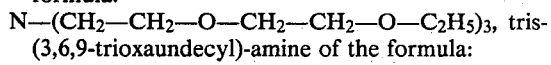
tris-(3,6-dioxanonyl)-amine of the formula:

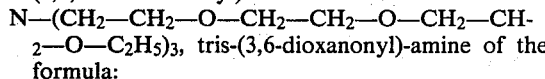
tris-(3,6,9-trioxadodecyl)-amine of the formula:

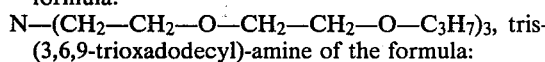
tris-(3,6-dioxadecyl)-amine of the formula:

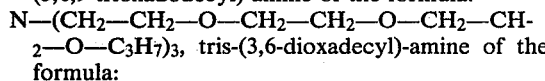
and tris-(3,6,9-trioxatridecyl)-amine of the formula:

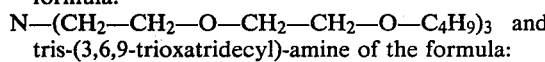

The following may also be mentioned: tris-(3,6-dioxa-4-methylheptyl)-amine of the formula:

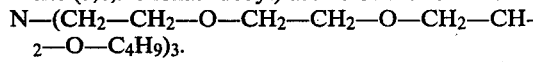

dioxa-2,4-dimethylheptyl)-amine of the formula:

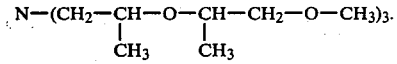

The amount of these derivatives is such that their molar proportion, relative to the reactant, is between about 0.5 and 15% and preferably between 1 and 10%.

The phosgenation is carried out in an organic solvent which is inert under the reaction conditions. Preference will be afforded to solvents having a relatively high b.p., in order to permit easy degassing of the excess phosgene, in particular aromatic solvents such as toluene or xylene, chlorinated aromatic solvents, such as chlorobenzene, aliphatic solvents, such as dodecane, or chlorinated aliphatic solvents, such as dichloroethane or trichloroethane.

The phosgenation can be carried out at a temperature between 0° C. and the b.p. of the reaction medium. However, as the reaction is rather slow by nature, it is advantageous to accelerate it by heating to a temperature between 60° and 130° C. and preferably to the reflux temperature. If the reaction is carried out at elevated temperature, it is advantageously carried out in an autoclave, at pressures which can range up to 5 bars (absolute pressure).

In practice, the solvent, the phosgene, preferably liquid phosgene, and the starting hydantoin are introduced into the reactor. Since the hydantoin is sparingly soluble in the medium, a suspension is obtained; this is heated and the acid acceptor is added thereto, if appropriate, in order to accelerate the reaction. Heating must be maintained for a sufficiently long time to complete the conversion. It has been found that heating times of 1 to 5 hours are suitable.

At the end of the reaction, there are two possible procedures. The first consists in isolating the intermediate chlorocarbonyl, the characteristics of which are given in an example below. It is found that the yield is virtually quantitative.

However, advantageously, when the process is used industrially, the organic solution of this intermediate can subsequently be used as such in the second stage, referred to as the condensation stage. In any case, even here, the medium must be cooled and the excess phosgene must be degassed before starting the second step.

The second step is much more rapid than the first and is carried out at a temperature ranging from 0° to 130° C., preferably from 20° to 80° C.

Stoichiometric amounts of the amine and then of an acid acceptor, respectively, are run into the chlorocarbonyl in an organic medium, it being possible for the acid acceptor to be of the same type as that used in the first step or to be the amine itself (in which case it is employed twice in the reaction) or also an inorganic base. After cooling and washing in an acid medium, and then removing the solvent, the expected N-substituted derivative is obtained with an excellent yield which can be above 90%.

The following examples are given by way of indication in order to illustrate the invention.

EXAMPLE 1

First step:

The following are run successively into a 1 liter five-necked reactor fitted with a condenser: chlorobenzene (300 ml) and then, whilst stirring, liquid phosgene (about 40 g, i.e. 0.4 mol) and, after stopping the stirring, 3-(3,5-dichlorophenyl)-hydantoin (61.3 g, i.e. 0.25 mol). The reactor is then heated at 75° C. for 1 hour, the liquid in the condenser being kept at a temperature which makes it possible to condense the phosgene. Triethylamine (25 g, i.e. 0.25 mol) is run into the reactor, cooled to about 30° C., in the course of 10 to 15 minutes. The temperature is kept at 130° C. for 3 hours 30 minutes, the liquid in the condenser being kept at a temperature which makes it possible to condense the solvent and to degas the hydrogen chloride.

Second step:

After the medium obtained in the first step has been cooled to 35° C., isopropylamine (14.7 g, i.e. 0.25 mol) and then triethylamine (25 g, i.e. 0.25 mol) are run in over a period of 15 minutes. The medium is heated at 75° C. for 20 minutes and then cooled to 20° C. 5% strength sulphuric acid (300 ml) is then run in and the mixture is stirred vigorously for 30 minutes. After separation of the aqueous phase by decantation, the chlorobenzene phase is washed with distilled water. The chlorobenzene layer is dried over anhydrous sodium sulphate and then concentrated under reduced pressure. This gives 80 g, i.e. a yield of 97%, a product of m.p. 130° C., containing 91.5% of 1-isopropylcarbamoyl-3-(3,5-dichlorophenyl)-hydantoin.

EXAMPLE 2

The procedure of the first stage of Example 1 is followed, except that the intermediate is isolated at the end of the reaction. This yields a white solid of m.p. 202° C., having the following percentage composition:

| %          | C     | H    | Cl    | N    | O     |
|------------|-------|------|-------|------|-------|
| calculated | 39.06 | 1.64 | 34.58 | 9.11 | 15.61 |
| found      | 39.09 | 1.45 | 34.24 | 9.18 | 15.62 |

Infra-red spectrographic analysis shows the existence of the bands at 1,830–1,820, 1,760 and 1,720 cm$^{-1}$ which are characteristic of carbonyl groups, corresponding to 1-chlorocarbonyl-3-(3,5-dichlorophenyl)-hydantoin.

EXAMPLES 3 TO 7

The procedure of Example 1 is followed, the isopropylamine being replaced in the second step by an equivalent amount of ethylamine, n-propylamine, aniline and dimethylamine, respectively. The yields and m.p. of the resulting products are indicated in the following table:

| HNR$_1$R$_2$ amine employed | M.p.    | Yield |
|-----------------------------|---------|-------|
| n-propylamine               | 92° C.  | 99%   |
| phenylamine                 | 182° C. | 99%   |
| ethylamine                  | 152° C. | 97%   |
| N,N—dimethylamine           | 162° C. | 98%   |

EXAMPLE 8

Use of isopropylamine as the acid acceptor.

A solution of isopropylamine (3.6 g, i.e. 0.06 mol) in chlorobenzene (20 ml) is run, in the course of 20 minutes, into a suspension of 1-chlorocarbonyl-3-(3,5-dichlorophenyl)-hydantoin (9.2 g, 0.03 mol), obtained in Example 2, in chlorobenzene (80 ml), the temperature being kept at 30° C. at the most. After stirring for one hour, chlorobenzene (150 ml) is added. The organic solution is washed with a 3.6% strength aqueous solution of hydrochloric acid (100 ml). After drying and concentrating under reduced pressure, 9.9 g of a solid of m.p. 135° C., corresponding to 1-isopropylcarbamoyl-3-(3,5-dichlorophenyl)-hydantoin, are obtained.

EXAMPLES 9 TO 13

An organic base (one mol, if appropriate with an excess) is run, at a temperature of 20° to 30° C., into a suspension of 3-(3,5-dichlorophenyl)-hydantoin (one mol) in a mixture, prepared beforehand, of phosgene (1.5 mols) in chlorobenzene (1,100 ml). The reaction medium is then heated for a certain time. In one of the experiments, the phosgenation was carried out in an autoclave at a pressure of about 3 bars. The resulting chlorocarbonyl is isolated. It is then used in the condensation reaction as described in Example 1.

The variable conditions of the phosgenation, and also the yields of intermediate chlorocarbonyl and of 1-isopropyl-3-(3,5-dichlorophenyl)-hydantoin, are recorded in the following table:

| Example No. | Acid acceptor | Auxiliary base | Temperature | Heating time in hours | Yield in mol %/reactant of chlorocarbonyl | of iprodione |
|---|---|---|---|---|---|---|
| 9 | TEA | — | 80° C. | 12 | 91 | 86 |
| 10 | DMAP | — | 100° C. | 5 | 91 | 82 |
| 11 | TEA (90%) | DMAP (10%) | 80° C. | 5 | 81 | — |
| 12 | Pyridine (10% excess) | — | 70–75° C. | 10 | 88 | — |
| 13 | Pyridine (under pressure) | — | 120–130° C. | 1 | 93 | 74 |

TEA = triethylamine
DMAP = dimethylaminopyridine.

EXAMPLE 14 a. Phosgenation 3-(3,5-Dichlorophenyl)-hydantoin (1 mol), disodium carbonate (2 mols), dimethylaminopyridine (0.09 mol) and chlorobenzene (1,100 ml) are introduced, at 20° C., into a reactor equipped with a condenser.

Phosgene (2 mols) is then run in.

The reaction mixture is subsequently heated at 80° C. for 1 hour 30 minutes and then at 105° C. for the same time. The inorganic substances are filtered off hot (110° C.) and the cake is washed with hot chlorobenzene (130° C.) (2×50 ml). This gives a suspension of 1-chlorocarbonyl-3-(3,5-dichlorophenyl)-hydantoin with a yield of this compound of 94%.

b. Condensation

This is carried out by following the procedure of Example 1 (second step).

Under these conditions, 1-isopropylcarbamoyl-3-(3,5-dichlorophenyl)-hydantoin is obtained with a yield of 92%.

EXAMPLE 15 a. Phosgenation 3-(3,5-Dichlorophenyl)-hydantoin (1 mol), disodium carbonate (2.5 mols) and tetrabutylammonium bisulphate (0.036 mol) are introduced into a reactor equipped with a condenser.

Phosgene (4 mols) is then run in and the reaction mixture is heated at 80° C. for 1 hour 30 minutes and then at 105° C. for 1 hour 30 minutes. The total amount of the suspended inorganic substances is filtered off hot (about 110° C.) and the cake is washed with chlorobenzene (2×50 ml) at 130° C.

b. Condensation

This is carried out by following the procedure of Example 1 (second step). The resulting product is isolated by evaporating off the solvent after acid and neutral washing of the chlorobenzene solution.

Under these conditions, a product containing 94% of 1-isopropylcarbamoyl-3-(3,5-dichlorophenyl)-hydantoin is obtained with a yield of 92%.

If this experiment is repeated using 0.018 mol instead of 0.036 mol of carbonate in the phosgenation, 1-isopropylcarbamoyl-3-(3,5-dichlorophenyl)-hydantoin is obtained with a yield of 80%.

We claim:

1. A process for the preparation, starting from 3-(3,5-dichlorophenyl)-hydantoin, of a compound of the formula:

$$\text{(I)}$$

in which
  R$_1$ is an alkyl radical containing from 1 to 4 carbon atoms or the phenyl radical and R$_2$ is a hydrogen atom or an alkyl radical containing from 1 to 4 carbon atoms, which comprises:
  in a first step, reacting phosgene with 3-(3,5-dichlorophenyl)-hydantoin in an inert organic solvent medium, in the presence of at least stoichiometric amount of acid acceptor, in order to form 1-chlorocarbonyl-3-(3,5-dichlorophenyl)-hydantoin, in accordance with the equation:

$$\text{(II)} \quad + \text{COCl}_2 \longrightarrow \quad + \text{HCl}$$

and,
  in a second step, reacting at 20°–80° C. the resulting product with a primary or secondary amine of the formula HNR$_1$R$_2$, in which R$_1$ and R$_2$ have the meanings indicated above, in an inert organic solvent, in the presence of an acid acceptor, in accordance with the equation:

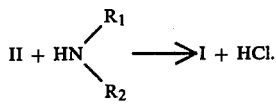

2. A process according to claim 1, wherein the first step of the reaction is carried out at a temperature between 0° C. and the b.p. of the reaction mixture.

3. A process according to claim 1, wherein the acid acceptor is a tertiary amine.

4. A process according to claim 3, wherein the acid acceptor is triethylamine.

5. A process according to claim 3, wherein the acid acceptor is pyridine.

6. A process according to claim 1, wherein the acid acceptor is an inorganic base.

7. A process according to claim 6, wherein the inorganic base is an alkali metal carbonate.

8. A process according to claim 1 wherein 0.5 to 15 mol % based on the acid acceptor of an auxiliary agent, selected from an auxiliary base different from said acid acceptor or a transfer agent, is used in said first step.

9. A process according to claim 8, wherein the auxiliary agent is an auxiliary base which is different from the acid acceptor.

10. A process according to claim 9, wherein the auxiliary base is chosen from the group comprising triethylamine, pyridine and dimethylaminopyridine.

11. A process according to claim 8, wherein the auxiliary agent is a transfer agent.

12. A process according to claim 8, wherein the transfer agent is a quaternary ammonium derivative of the formula:

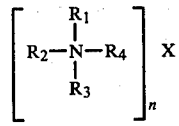

in which: $R_1$, $R_2$, $R_3$ and $R_4$, which are identical or different, each represent an alkyl radical containing from 1 to 20 carbon atoms, a cycloalkyl radical containing from 3 to 6 carbon atoms, an alkenyl radical containing from 2 to 20 carbon atoms, a hydroxyalkyl radical containing from 1 to 20 carbon atoms or an optionally substituted phenylalkyl radical in which the alkyl part contains from 1 to 6 carbon atoms, X represents a chlorine, bromine or fluorine atom or an $SO_4$, $SO_4H$, $PO_4H_2$ or hydroxyl radical, an alkoxysulphonyloxy radical containing from 1 to 4 carbon atoms, an alkanesulphonyloxy radical containing from 1 to 4 carbon atoms, an arenesulphonyloxy radical or an alkanoyloxy radical containing from 1 to 4 carbon atoms and n is a number equal to the valency of X.

13. A process according to claim 12, wherein the quaternary ammonium derivative is tetrabutylammonium chloride or bisulphate.

14. A process according to claim 11, wherein the transfer agent is a phosphonium derivative of the formula:

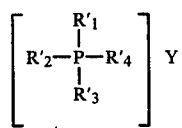

in which: $R'_1$, $R'_2$, $R'_3$ and $R'_4$, which are identical or different, each represent an alkyl radical containing from 2 to 8 carbon atoms and Y represents a chlorine or bromine atom.

15. A process according to claim 11, wherein the transfer agent is a sequestering agent of the formula:

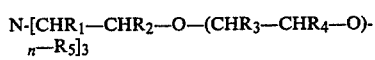

in which: n is an integer which is greater than or equal to 0 and less than or equal to about 10 ($0 \leq n \leq 10$), $R_1$, $R_2$, $R_3$ and $R_4$, which are identical or different, represent a hydrogen atom or an alkyl radical having from 1 to 4 carbon atoms, and $R_5$ represents an alkyl or cycloalkyl radical having from 1 to 12 carbon atoms, a phenyl radical or a radical $-C_mH_{2m}-\phi$ or $C_mH_{2m+1}-\phi-$, in which m is between 1 and 12.

16. A process according to claim 15, wherein the inorganic base is associated with tris-(3,6-dioxaheptyl)-amine.

17. A process according to claim 1, wherein, in the second step, the amine $HNR_1R_2$ is also used as the acid acceptor.

18. A process according to claim 1, wherein the solvent for both steps is an aromatic solvent.

19. A process according to claim 17, wherein the solvent is chlorobenzene.

20. A process according to one of claims 3 and 6, wherein the solvent for both steps is an aliphatic solvent.

21. A process according to claim 2, wherein the first step is carried out at a temperature of 60° C. to 130° C.

22. A process according to claim 21, wherein the reaction is carried out under an absolute pressure of 1 to 5 bars.

23. A process according to claim 1, wherein the two steps are carried out continuously in a single solvent, with any excess phosgene being degassed at the completion of said first step.

24. A process according to claim 1, wherein the intermediate is separated off at the end of the first step.

25. A process according to claim 1, wherein the acid acceptor is triethylamine or pyridine, and wherein the two steps are carried out continuously in the same solvent, with any excess phosgene being degassed at the completion of said first step.

* * * * *